United States Patent
Chu et al.

[11] Patent Number: 6,110,480
[45] Date of Patent: *Aug. 29, 2000

[54] METHOD FOR PREPARING AN ENVIRONMENTALLY COMPATABLE POROUS MATERIAL COMPRISING BENEFICIAL NEMATODES AND THE BIOTIC PREPARATIONS PRODUCED THEREFROM

[75] Inventors: Linag-Kuang Chu; Chiao Po Lin; Chien-Ming Shih; Tsae Yueh Lee; Tai-Sen Soong, all of Taipei, Taiwan

[73] Assignee: Development Center for Biotechnology, Taipei, Taiwan

[*] Notice: This patent issued on a continued prosecution application filed under 37 CFR 1.53(d), and is subject to the twenty year patent term provisions of 35 U.S.C. 154(a)(2).

[21] Appl. No.: 08/955,114

[22] Filed: Oct. 21, 1997

[51] Int. Cl.$^7$ ............... A01N 25/00; C12N 5/00
[52] U.S. Cl. ............ 424/405; 800/2; 800/DIG. 5; 119/6.5; 119/6.6; 119/6.7
[58] Field of Search ................... 424/405, 406, 424/489, 409; 800/2, DIG. 5; 119/6.5, 6.6, 6.7

[56] References Cited

U.S. PATENT DOCUMENTS

| | | | |
|---|---|---|---|
| 4,334,498 | 6/1982 | Bedding | 119/1 |
| 4,615,883 | 10/1986 | Nelsen et al. | 424/84 |
| 5,042,427 | 8/1991 | Bedding | 119/6.7 |
| 5,113,799 | 5/1992 | Carr et al. | 119/6.5 |
| 5,183,950 | 2/1993 | Popiel et al. | 800/2 |

FOREIGN PATENT DOCUMENTS

| | | |
|---|---|---|
| 8503412 | 8/1985 | WIPO. |
| 8808668 | 11/1988 | WIPO. |
| 8904602 | 6/1989 | WIPO. |

OTHER PUBLICATIONS

Edward J. Buecher and Irene Popiel, "Liquid Culture of the Entomogenous Nematode *Steinerema feltiae* with Its Bacterial Symbiont", Journal of Nematology 21(4): p. 500–504, 1989.

*Primary Examiner*—John Kight, III
*Assistant Examiner*—Charanjit S. Aulakh
*Attorney, Agent, or Firm*—McDonnel Boehnen Hulbert & Berghoff

[57] ABSTRACT

The present invention teaches method for culturing nematode pesticidal compositions, to produce at a high yield, and generate biotic compositions that are effective as insecticides with high pesticidal activity and preventive effects.

20 Claims, 1 Drawing Sheet

METHOD FOR PREPARING AN ENVIRONMENTALLY COMPATABLE POROUS MATERIAL COMPRISING BENEFICIAL NEMATODES AND THE BIOTIC PREPARATIONS PRODUCED THEREFROM

FIELD OF THE INVENTION

The invention relates to a method for preparing an environmentally compatible porous material comprising beneficial nematodes with pesticidal activity, and to the biotic preparations produced therefrom and to the use for controlling pests.

BACKGROUND OF THE INVENTION

The present invention relates to a process for preparing an environmentally compatible porous material comprising beneficial nematodes with insecticidal activity, and to the biotic preparations produced therefrom. The environmentally compatible porous material may be directly applied to the desired target to eliminate the recovery procedures and formulation steps involved in currently used methods.

Nematode worms (Class Nematoda) have round elongated bodies that usually taper at the ends to almost a point. Unlike flat worms (Playtyhelminthes), nematodes have no cillia, the body being enclosed in a cuticle coat which, combined with the absence of circular muscles, severely limits the types of movements the nematodes can make, thus they appear to thrash about in an almost random fashion. Nematodes are extremely abundant, and occur in almost every type of habitat, with many free-living in soil or water, and are generally microscopic in size. Certain parasitic nematodes, of both plants and animals, can attain a length of up to one meter. Nematodes are continuous feeders, requiring an essentially unlimited source of food as they lack the ability to store food. (see generally Keeton (1980) *Biological Science* 3$^{rd}$ Edition, WW Norton & Co., New York).

The nematode-based pesticide of the present invention is not a nematicide (i.e. toxic to nematodes) but a kind of novel pesticide/biotic preparation which comprises beneficial nematodes associated with symbiotic bacteria in a biodegradable matrix which is useful for controlling pests that would harm cultivated plants. A nematode-based pesticide of the present invention has several advantages over typical chemical pesticides. For instance, general chemical pesticides are highly toxic, pesticide poisonous, and easy to result in environmental pollution; they affect natural predators, destroy ecological balance, and often cause the resistance against the targeted pests.

U.S Pat. No. 4,334,498 (this and all subsequent patent documents are hereby incorporated by reference in their entirety) disclosed a method for rearing nematodes using an assemblage for rearing nematodes comprises a growth medium suitable for the culture of the nematodes, the growth medium being dispersed to allow free movement of fluids over the surface of the medium and to maximize the ratio of the surface area of the medium to volume of the assemblage. The assemblage may comprise an animal tissue homogenate as growth medium dispersed over the surface of elements of inert material such as wood-wool or crumbed plastics foam.

U.S Pat. No. 4,334,498 describes that infective larvae of *Neoaplactana carpocapsae* have been observed to destroy a wide range of insect pests under laboratory conditions. This ability is accounted for by the nematode's own pathogenicity towards the insects, and by its association with the symbiotic bacterium, *Achromobacter nematophilus*, which is usually to be found in the intestinal lumen of infective species. Following ingestion by an insect, the nematode will usually penetrate the gut wall to enter the haemocoel and release *A. nematophilus* which mutliply and lead to the death of the host by septicaemia. Additionally, there will often be reproduction of the nematodes in the dead host and hence generation of further infective organisms. The patent discloses that infective nematodes will remain active for substantial periods of time in the absence of free water, provided their body moisture, oxygen supply and mobility can be maintained, and that this can be achieved by use of oil instead of water as a medium in which to store or disperse the nematodes. Thus the commonly practiced techniques for rearing nematodes are mostly based upon solid and liquid culture.

The compositions and method of the instant invention teaches a process for preparing nematode-based pesticide suitable for mass production and the formulation of preparations which will be suitable for long-term storage, for example for a time of more than six months. Because nematodes are multicellular animals, the preparations currently practiced are not suitable for prolonged storage, such as would be possible with other microbiotic preparations (such as storage for one year or more). It is recognized in the art that it would be most useful to have preparations of nematodes which could be stored for a period of time prior to use. For instance, WO 89/04602 and U.S. Pat. No. 4,615,883 describe a method and composition for an insecticide comprising a hydrated hydrogel capsule containing an insecticidally effective amount of at least one nematode capable of infecting an insect host, which capsule has sufficient hydration to maintain the viability and infectivity of said nematode. Also disclosed are methods for providing said insecticidal compositions. The method disclosed utilizes alginate to embed nematodes, and such preparations can be used for 3 to 6 months. However, one difficulty in using preparations such as this, is that it has to dissolved in sodium citrate (taking about 30 minutes), and then diluted with water before spraying onto crops.

The methods described in U.S. Pat. No. 4,334,498 and WO 88/08668 use the principle of nematode cryptobiosis, to carry out the dehydration of nematodes under conditions for decreasing relative humidity in a stepwise manner, to make the nematode preparations into essentially clays. The storage of the clay obtained may be suitable for 3 to 6 months under refrigerated conditions. U.S. Pat. No. 5,042,427 describes methods to transport entomopathogenic nematodes. It is described how it is necessary to store them in a manner such that a significant proportion of them survive after being stored and are reactivated when dispersed in water. The process provides storage by mixing an aqueous cream of clean third stage infective juveniles (J3) of nematodes with clay. The clay may be in chip form, or calcined, milled and sieved, but comporises from about 33 percent (by weight) to 67 percent (by weight) of the homogeneous mixture.

However, the clay process is commercially expensive to practice as it spends a great deal of time and energy in the dehydration procedure. Unfortunately, the clays must be extensively pretreated prior to use, as they have to be treated at high humidity (95% relative humidity) overnight to rehydrate the nematodes. In addition, the clays produced by this procedure, and the dust associated with these products are harmful to the lungs of humans.

U.S. Pat. No. 5,113,799 discloses an apparatus for the rearing of insects and the production of insect related products, primarily insect viruses and parasites commonly used for the control of insect pests. The apparatus comprises an environmental control system, a sealed enclosure consisting of a hood and a base, and a system of vertically supported food leaves.

U.S. Pat. No. 5,183,950 relates to methods to desiccate, package, store, and ship insect parasitic nematodes in both large and small quantities while maintaining their viability and pathogenicity to insects. In particular, to maintain the infective juveniles of the Steinernematid and Heterorhabditid nematodes in a state of dormancy so that their food reserves are not used up, and so that upon return to suitable conditions they revive and remain pathogenic to the insect host. In short, the methods and containers disclosed are designed to maintain the infective juveniles in a "cryptobiotic" state—a state of dormancy in which metabolism is suppressed. Several ways of doing this, with varying degrees of success, are +PG,6 known for organisms in general. The most generally suggested method and perhaps the most universally applicable is the induction of cryobiosis, i.e., reduced metabolism at low, usually freezing temperatures. In addition, and more difficult to achieve, are anhydrobiosis, which is induced by evaporative desiccation and the closely related osmobiosis, which is induced by osmotic desiccation.

PCT Application WO 85/03412 suggests methods of transport and storage which depend on maintaining putative anaerobic conditions and the presence of an antimicrobial agent. High osmotic strength solutions are also used to prevent bacterial growth. The proposed storage conditions also include an adsorbent such as charcoal or synthetic resins, although it is not clear what these agents are expected to adsorb. The disclosure exemplifies the use of formaldehyde as an antimicrobial, and proposes storage containers which contain both the nematodes and adsorbent charcoal.

T. N. Wang et al in Sugar Research Institute (1992) had reported that they utilize sugar dregs to absorb nematode infected liquid and apply them to the field. (The nematodes of this preparation may be stored at room temperature for about one month.) However, the use of bagasse as the matrix for culturing nematodes (adding culture medium) is not disclosed in the article. In addition, the bagasse will be easily attacked by fungi due to sugar residue.

Formulation and application technology in "Entomopathogenic Nematodes in Biological Control" Georgis. R. describes that vermiculite and peat can be used as moistened carriers for transporting and storing nematodes. However, the nematodes are taught to be cultured and recovered prior to applying vermiculite and peat. As described above, the recovery step is cost-consuming, and loss in nematode yield and the problem of waste water are great disadvantages to this method of transport. In addition, Georgis did not use vermiculite or peat as support medium for culturing nematodes.

Thus the present methods for preparation of nematode based insecticide preparations are cumbersome and labor-intensive, and do not afford effective long-term storage of viable materials. In contrast, the present invention teaches simplified and efficient methods for producing biodegradeable and bio-compatible biotic constructs useful for the long-term storage of nematode/bacterial preparations, and useful for the simplified application to subject plants.

SUMMARY OF THE INVENTION

It is an object of the present invention to provide a biotic preparation for controlling insect comprising an environmentally compatible porous material containing beneficial nematodes with pesticidal activity in which the entomogenous nematodes are obtained by being incubated with symbiotic bacteria and the nematode source in the porous material containing suitable production medium.

It is an other object of the present invention to provide a process for preparing an environmentally compatible porous material containing beneficial nematodes with pesticidal activity comprising inoculating symbiotic bacteria and a nematode source into or on the porous material containing suitable nutrient supportive medium.

It is a futher object of the present invention to provide a method for controlling pests comprising treating the desired target, with an environmentally compatible porous material containing beneficial nematodes with pesticidal activity.

DETAILED DESCRIPTION OF THE INVENTION

Figure 1:
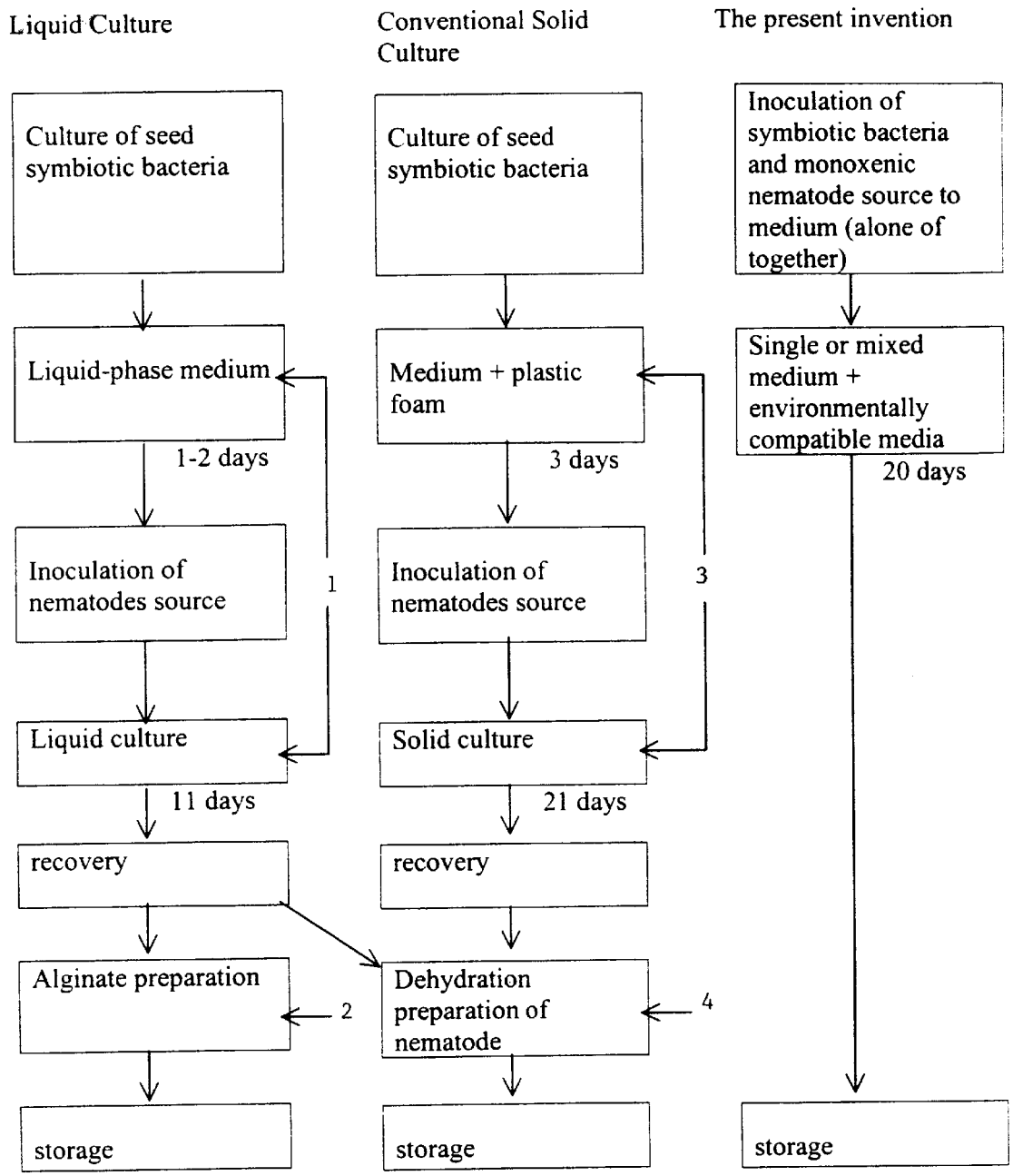
FIG. 1 is a diagram which describes the schemes of the methods used by conventional liquid culture and solid culture in comparision with the process of the invention for preparing pesticidal preparations.

Beneficial nematodes which are suitable for use in a nematode-based pesticide of the present invention include Rhabditidae, Steinernematidae and Heterorhabditidae. However, other suitable nematodes can be used provided that they act to kill infected hosts in association with symbiotic bacteria. In a preferred embodiment the nematode is Rhabditida.

Nematodes have a simple life cycle comprising the egg, 4 larvae stages and adult. The infective stage is termed the "stage 3 infective juvenile" (J3), or also known as the "infective juvenile" (IJ). IJs are especially resistant to environmental conditions, and enter into hosts through the openings in the body of hosts, such as mouth, anus or respiration pores. After infection, the insecticidal course is generally the same for all infected pests, but may vary depending upon the host pest. The infective nematode will actively penetrate the gut wall or trachea of the pest and enter the hemocoel, whereupon the symbiotic bacteria, such as Xenorhabdus, will be released into the body cavity of the host pest. The symbiotic bacteria will rapidly multiply in the host body. The host will die from septicemia in about 48 hours. After ingesting bacterial cells and tissues of the host, the immature nematode will develop into an adult.

The beneficial nematodes are harmless to plants and safe to human beings and domesticated animals. In 1987, the Environmental Protection Administration of United States had established that biotic preparations comprising Steinernema and Heterorhabditis and symbiotic bacteria thereof may be not necessary for the statutory requirement of FIFRA Section 25(b)(1). They are commercially available and have not been registered in many countries. They have no effects on the other non-targeted arthropods in soil, and there is no evidence of the development of resistance by pests.

In general, the processes for producing a nematode-based insecticide are more complicated than procedures for fermenting general microorganisms, because of the stringent requirements for cultivating using sterile source material and the mixed cultivation of nematode with their biosymbiotic bacteria. Because nematodes are multicellular animals, the cultivation periods are longer than those of cultivating other microorganisms (for example, it takes 11 and 21 days for the liquid and solid culture, respectively). The processes used also require additional steps for each procedure, from harvesting to storage and refrigeration. In particular, the recovery step is complicated and labor intensive, and results in the loss of nematode yield. In addition, the recovery step yields waste water which must be disposed of safely. Because of the long cultivation period of nematodes, and the labor-intensive harvesting procedure, the cost for production is quite high. Thus, the cost of nematode-based pesticidal biotic preparations tends to be high, and the price of such products are quite expensive. Furthermore, the traditional methods for producing nematode-based insecticide in conventional culture require two separate steps of cultivating symbiotic bacteria in one culture, and then inoculating nematodes in medium, followed by incubation before recovery procedure. Such multi-step cultivation, especially for solid culture, in comparison with one-step method for cultivating symbiotic bacteria and inoculating nematodes in medium.

The matrix support of the biotic constructs of the present invention can be of a suitable porous material or combination of materials, such that the material(s) contains many pores. The porous materials used herein include environmentally compatible porous material (for example, vermiculite) or bio-decompositable biodegradeable porous material (for example, sugar dregs, sponge, loofah, etc.), all of which are useful in mass production of the biotic constructs of the present invention. The environmentally compatible biotic constructs of the present invention can be used without causing extensive environmental contamination or poisoning of the ecosystem. The biodegradable biotic constructs of the present invention are decompositable or destructible by microorganisms or organisms occurring in the nature. The biotic compositions of environmentally compatible porous material can be in the form of a granule, sheets of material, strands of material, or any other suitable shape which allows for application to a planted field.

The biotic constructs of the present invention are useful for controlling pests, which includes repulsion and destruction of such targeted pests. Repulsion refers to the impact on targeted insects or slugs which causes them to flee away from the treated plants without causing any significant damage. Destruction refers to the killing of the insect hosts or slugs, or the inhibition or termination of further reproduction of such targeted pests.

The present invention may be better understood and illustrated by the following illustrative examples which are meant by way of illustration and not limitation.

Example Materials and Methods

Tested nematodes: *Steinernema carpocapsae* (SC) strain A11 (SCA). The monoxenic nematodes used as the source of cultivated nematodes were obtained by the method disclosed in Edward J. and Irene Popiel in Jounnal of Nematology 21(4):500–504, 1989. After the in vivo culture in silkworm or tobacco cutworm, isolated nematode was stored at 10° C.

Tested bacteria: the symbiotic bacteria isolated from the intestinal tract of SCA, and was identified by Food Science & Technology Research Institute (Taipei, Taiwan ROC) as *Xenorhabdus nematophilus*. Isolated baceria was stored at −70° C.

The composition of TSA (Tryptic Soy Agar) is as follows:

| TSA (Difco) | 40 g |
| distilled water | 1 L |

The composition of YS is listed as follows:

| $K_2HPO_4$ (Merck) | 0.5 g |
| $NH4.H_2PO_4$ (Sigma) | 0.5 g |
| $MgSO_4.7H_2O$ (Merck) | 0.2 g |
| NaCl (Merck) | 5.0 g |
| yeast extract (Merck) | 5.0 g |
| distilled water | 1 L |

The composition of production medium (PM) is listed as follows:

| Chicken egg (ordinary supermarket) | 180 g |
| vitayeast powder (Taiwan Sugar Corp.) | 15 g |
| Salad oil (Taiwan Sugar Corp.) | 75 g |
| distilled water | 1 L |

The sequential procedure of cultivating the symbiotic bacteria was performed as follows: resuspending the bacteria at −70° C., in TSA; incubating at 28° C. for 24 hours; incubation in YS liquid medium for 16 hours (at 25° C., 150 rpm shaker, in 30 ml/125 ml flask). The bacteria culture is then thoroughly mixed with monoxenic nematode source, as described in Edward J. and Irene Popiel in Jounnal of Nematology 21(4):500–504, 1989, to form a uniform mixture.

In a prefered embodiment, to form the biotic construct of the present invention, the bacteria/nematode mixture described above is then inoculated into an environmentally compatible porous material which has been pre-treated with suitable nutrient production medium, autoclaved at 121° C. for 30 min in a covered vessels. It is also possible to inoculate the pretreated support matrix with bacteria and nematode from separate sources.

The inoculated biotic construct is then incubated for a period of time sufficient to allow the inoculated nematodes to populate the porous support matrix material (typically about 15–21 days) at 25° C. The resultant biotic composition is an environmentally compatible porous material comprising a population of nematodes therein, and the symbiotic bacteria.

The environmentally compatible biotic composition can be applied directly to the desired target, such as a field, grass, plants, etc. for controlling pests.

Insect for Bioassay: 4th instar Tobacco cutworm (*Spodoptera litura*).

Method for Toxicity Bioassay: Petri-disk and filter paper method disclosed in Jennifer L. Woodring et al, 1988. The ratio of nematodes to insects about 25:1.

The plastic sponge (2×2×2 cm³) used in the tests was made of polyether polyurethane, which might be autoclaved and purchased from commercial sources (Jih-Hung Sponge Inc., Taipei, Taiwan ROC).

The vermiculite (No.2), and pearlite (No.2), used in the tests were all commmercially purchased (Nan-Hei Vermiculite Corp., Taipei, Taiwan ROC).

The glass containers used in the coincubation steps of nematodes and symbiotic bacteria were all equipped by a 50 ml flask(Pyrex) with sponge or 1 to 2 g porous material described such as vermiculite or pearlite.

EXAMPLE 1

The Solid-phase Cultivation of SCA in Different Materials

In this example vermiculite, pearlite and foam sponge ("sponge") were used as the environmentally compatible, solid support matrix porous material, and the ratio of materials used is listed in Table 1. To each support, approximately 10% symbiotic bacteria (i.e. 2 ml of culture), and approximately 1×10$^4$ monoxenic SCA were inoculated. After 14 days, the yields and the insecticidal activity of the prepared biotics were determined, and the results are also listed in Table 1.

TABLE 1

The effects on solid-phase cultivation of SCA in different materials

| materials | weight (g) | medium (ml) | inoculated nematode | yield (10$^4$/ml) | Proliferation fold |
|---|---|---|---|---|---|
| vermiculite | 2.0 | 8 | 1000 | 5.7 | 450 |
| pearlite | 2.0 | 8 | 1000 | 5.3 | 450 |
| sponge | 0.9 | 8 | 1000 | 20.0 | 1600 |
| sugar dregs | 1.0 | 7 | 1000 | 8.7 | 610 |

EXAMPLE 2

The Cultivation of Beneficial Nematodes in Environmentally Compatible Porous Material (such as vermiculite)

A 14L vessel charged with 600 g of vermiculite and 3000 ml of PM was autoclaved for 30 minutes, then were inoculated with 300 ml of symbiotic bacteria and 2 million monoxenic SCA. After being cultured for 20 days at 25° C., the yield and pesticidal activity were determined. The results are listed in Table 2.

TABLE 2

| vessel volume | yield (10$^4$/g vermiculate) | insecticidal activity |
|---|---|---|
| 14 L | 29.5 | 100 |
| flask | 30.0 | 95 |

EXAMPLE 3

Evaluations of the Biological Control on Larvae of Tobacco Cutworm by SCA Presented in Vermiculite Preparation in the Pot Test Period of test: 17 days Testing place: the 6th balcony of Developmental Center of Biotechnology (DCB, 81 Chang Hsing Street, Taipei, Taiwan ROC).

Tested nematodes: SCA$_1$ which were cultured in vermiculate and PM medium.

Insects to be tested: the fourth instar of *Spodoptera litura* Fabricius (tobacco cutworm) which were provided by Professor Shih Cheng-jen (Department of Botanical Blight, National Taiwan University, Taipei, Taiwan ROC).

Grass to be tested: *Cynodon spp.* D. W., strain 419 and strain 328, obtained from the construction site of Putting Greens in Lung T'an and Yang-Sneng golf course (Yang Mei, Taiwan ROC) respectively.

Pot: 20.5 ×13.5 ×7.5 cm$^3$, area 276.75 cm$^3$.

Design of test: completely random design (CRD) was taken and repeated 4 times.

Application dosage: 2.4 billion nematodes/ha (hectacare), 1.2 billion nematodes/ha., 0.6 billion nematodes/ha.

Each pot of grass was close cut 2 days before applying the worms. Twenty plantlets, randomly selected, were examined in each pot. The bite trace numbers on the top 6 leaves of each plantlet was calculated as the number of affected grasses and leaves.

Every pot of grass was irrigated with 400 ml running water before the application of the pesticide and worm, and was irrigated with 150 ml running water after the application to facilitate the release of nematode SCA from vermiculite. The results are listed in Table 3.

TABLE 3

The effects of the biological controlling on tobacco cutworm by SCA cultured in vermiculite in the pot test

| Treatment dosage (per hect) | repeat | no. of damaged leaves | XDS % | number of damaged grass | XDS % |
|---|---|---|---|---|---|
| 2.4 × 10$^9$ | 1 | 1 | 42.4 b 3.3 | 1 | 21.5 c 10 |
| | 2 | 5 | | 2 | |
| | 3 | 2 | | 1 | |
| | 4 | 6 | | 4 | |
| 1.2 × 10$^9$ | 1 | 13 | 143.4 b 11.7 | 12 | 82.6 b 40 |
| | 2 | 10 | | 6 | |
| | 3 | 13 | | 8 | |
| | 4 | 15 | | 7 | |
| 0.6 × 10$^9$ | 1 | 43 | 3711.2 a 30.8 | 13 | 143.7 a 70 |
| | 2 | 38 | | 14 | |
| | 3 | 21 | | 9 | |
| | 4 | 46 | | 15 | |
| 0 (Control) | 1 | 15 | 3112.9 a 25.8 | 8 | 143.9 a 65 |
| | 2 | 44 | | 17 | |
| | 3 | 26 | | 14 | |
| | 4 | 38 | | 15 | |

Data was analyzed by One Way ANOVA and tested by Duncan's Multiple Range test. The different numbers after means represent the significant difference between treatments ($p=0.05$).

The numbers of damaged leaves and grasses were calculated by random selection of 20 plantlets and the top 6 leaves of each plantlet examined, so the total number of leaves to be calculated was 120 leaves/per pot.

Results (I) As shown in Table 1, a high yield of viable nematode can be obtained when using porous materials for support and cultivation. The yield obtained by using sponge as culture material was the highest.

(II) As shown in Table 2, the addition of symbiotic bacteria facilitated mass rearing of nematode SCA. The yield of culture was 1.2 billion/vessel. The pesticidal activity at day 5 was 95%.

(III) The efficacy of the biotic composition for the biological control of tobacco cutworm by SCA cultured in vermiculite in the pot test were as follows:

As shown in Table 3, the treatment at 2.4×10$^9$/ha and 1.2×10$^9$/ha were significantly better than that of 0.6×10$^9$/ha and control. For the damage of grass, the most effective pesticidal controlling doses were 2.4×10$^9$/ha 1.2×10$^9$/ha 6×10$^8$/ha. Nematode SCD$_1$ presented in vermicon (vermiculite) preparation demonstrated efficacy in preventing cotton leafworm destruction of grass lawn.

Significantly, the storage for the biotic preparations of the present invention have been tested to be more effective, after more than 6 months under refrigerated condition.

These Data demonstrate that the method for culturing nematode of the present invention, produce at a high yield, and generate biotic compositions that are effective as insecticides with high pesticidal activity and preventive effects, which can be stored for at least 6 months under refrigerated conditions.

What is claimed is:

1. A biotic preparation for controlling pests comprising an environmentally compatible porous material containing beneficial nematodes with pesticidal activity, wherein said nematodes are obtained by cultivation with symbiotic bacteria.

2. A biotic preparation of claim 1, wherein said environmentally compatible porous material is vermiculite, peat or pearlite.

3. A biotic preparation of claim 1, wherein said environmentally compatible porous material is biodegradeable.

4. A biotic preparation of claim 1, wherein said environmentally compatible porous material is in the form of a granule.

5. A biotic preparation of claim 1, wherein said symbiotic bacteria is Xenorhabdus or Photorhabdus.

6. A biotic preparation of claim 1, wherein said nematode is from a monoxenic or sterilized source.

7. A biotic preparation of claim 1, wherein said nematode is selected from the group consisting of Rhabditidae, Steinernematidae and Heterorhabditidae.

8. A biotic preparation of claim 1, wherein said nematode is *Steinernema carpocapsae*.

9. A method for preparing an environmentally compatible porous material containing entomogenous nematodes with pesticidal activity comprising inoculating symbiotic bacteria and a nematode source to a porous material with a suitable nutrient production medium.

10. The method of claim 9, wherein said environmentally compatible porous material is vermiculite or pearlite.

11. The method of claim 9, wherein said environmentally compatible porous material is biodegradable.

12. The method of claim 9, further comprising the step of mixing symbiotic bacteria and the nematode source to form a mixture prior to inoculation of the porous material.

13. The method of claim 9, wherein said symbiotic bacteria is Xenorhabdus or Photorhabdus.

14. The method of claim 13, wherein said xenorhabdus is *Xenorhabdus nematophilus*.

15. The method as defined in claim 9, wherein said nematode is from a monoxenic or sterilized source.

16. The method as defined in claim 9, wherein said nematode is selected from the group consisting of Rhabditidae, Steinernematidae and Heterorhabditidae.

17. The method as defined in claim 9, wherein said nematode is *Steinernema carpocapsae*.

18. A method for controlling pests comprising treating the desired target to be kept free from the pests with an environmentally compatible porous material containing beneficial nematodes with pesticidal activity.

19. A method as defined in claim 18, wherein said environmentally compatible porous material is in the form of a granule.

20. A method as defined in claim 18, wherein said target is selected from the group consisting of grass, field, pot and lawn.

* * * * *